United States Patent [19]

Cooper

[11] Patent Number: 4,847,130

[45] Date of Patent: Jul. 11, 1989

[54] TAG ATTACHMENT SYSTEM

[75] Inventor: Michael J. Cooper, Colchester, Great Britain

[73] Assignee: Denny Bros. Printing Limited, Suffolk, England

[21] Appl. No.: 92,877

[22] Filed: Sep. 3, 1987

[51] Int. Cl.[4] ........................ A61F 13/02; B32B 3/10; B32B 7/06; G09F 3/00

[52] U.S. Cl. ........................ 428/40; 428/131; 428/202; 40/310; 156/249

[58] Field of Search ............... 156/540, 542, 541, 361, 156/230, 238, 241, 249, 293, DIG. 6, DIG. 7, DIG. 14, 289, 247, 448; 428/131, 132, 134, 138, 200, 202, 352, 914, 40, 194, 198; 40/310, 311

[56] References Cited

U.S. PATENT DOCUMENTS

| | | | |
|---|---|---|---|
| 3,149,431 | 9/1964 | Blish | 40/310 |
| 3,884,443 | 5/1975 | McMaster | 428/352 |
| 4,019,935 | 4/1977 | Harvey | 156/361 |
| 4,050,457 | 9/1977 | Davidson | 428/40 |
| 4,208,819 | 6/1980 | Jones et al. | 40/310 |
| 4,399,178 | 8/1983 | Barta | 156/238 |
| 4,581,266 | 4/1986 | Magnotta | 428/352 |

FOREIGN PATENT DOCUMENTS

| | | | |
|---|---|---|---|
| 1361007 | 12/1964 | France | 40/310 |

*Primary Examiner*—Robert A. Dawson
*Assistant Examiner*—Louis Falasco
*Attorney, Agent, or Firm*—Wenderoth, Lind & Ponack

[57] ABSTRACT

The present invention is drawn to a tag attachment system from which tags are suppliable to necked articles and the method associated with the tag attachment system for supplying tags to necked articles. A carrier strip of material has pressure-sensitive adhesive disposed on a surface thereof. A plurality of tags are releasably secured to the strip at the surface of the strip and the tags are spaced apart along the length of the strip. Each of the tags has a surface on which a layer of coating release material is disposed and an aperture in which the necks of necked articles are receivable. The surface of the tags on which the coating release material is disposed confronts the surface of the carrier strip on which the adhesive is disposed so as to facilitate the releasable securement of the tags to the strip. The strip is passed around a guide disposed adjacent a path along which a plurality of necked articles are traveling. As the strip travels around the guide, the tags separate from the strip and the apertures therein are consecutively disposed in the path adjacent the necks of the articles whereupon the same are received by the necks of the articles resulting in the looping of the tags over the articles.

8 Claims, 2 Drawing Sheets

TAG ATTACHMENT SYSTEM

BACKGROUND OF THE INVENTION

This invention relates to a tag attachment system for the attachment of tags to the necks of bottles and similar necked articles by mechanical means.

SUMMARY OF THE INVENTION

According to this invention, there is provided a tag attachment system comprising a carrier strip having adhesive on one surface thereof and a plurality of tags releasably secured at spaced intervals along the length of the strip by said adhesive, each tag having an aperture adjacent one end thereof for facilitating the engagement thereof about the neck of a necked article, the face of the tag facing said one surface having thereon a coating of release material, and the areas of the strip not covered by the tags not being adhesive.

According to a preferred embodiment of the invention, the end of each tag remote from said one end has means by which said remote end can be adhesively secured to the article. Preferably said means comprises a portion at said remote having a surface of facing the strip and carry an adhesive operative to releasably secure said portion to the strip.

The tag may have a folded leaflet attached thereto. The leaflet may be held closed against the tag by a cover sheet detachably secured to the tag at opposite ends of the folded leaflet.

The invention also provides a method of attaching tags to the necks of respective necked containers moving in succession along a flow path with the necks of the containers projecting at right angles to the flow path, comprising the steps of feeding a carrier strip, in the same general direction as the movement of the containers, along a path which is inclined towards the tops of the necks of the containers deposing, at a location adjacent the flow path of said tops, a guide from which the strip moves in a direction generally opposite to the direction of movement of the containers. The strip has adhesive on a surface thereof remote from the guide and a plurality of said tags releasably secured thereto at intervals spaced along the length of the strip by said adhesive. Each tag has a hole therein adjacent its leading end with respect to the movement of the strip for receiving the neck of a container. The face of each tag facing said surface of the strip has thereon a coating of a release material, and the areas of the strip not covered by the tags are not adhesive. Thus, the leading end of each tag as it comes to the guide peels from the strip so that the hole thereof is in the path of movement of and receives the top of the neck of one of the containers and the tag becomes attached to the container.

BRIEF DESCRIPTION OF THE DRAWINGS

The invention will now be described in more detail with reference, by way of example, to the accompanying drawings in which.

DETAILED DESCRIPTION OF THE PREFERRED EMBODIMENTS

Figure 1:
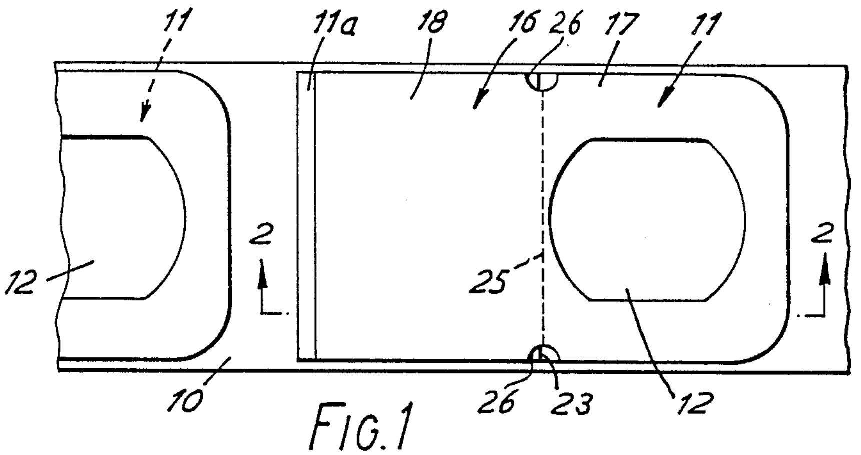
FIG. 1 is a plan view of a tag application system according to the invention.
Figure 2:
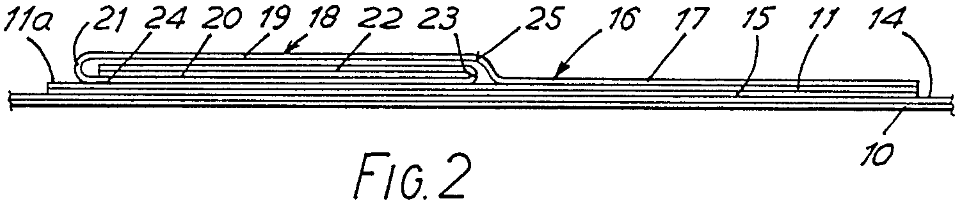
FIG. 2 is a sectional view on line 2—2 of FIG. 1.

Referring to FIGS. 1 and 2, the system employs a carrier strip 10 for carrying a succession of tags 11 each formed with an aperture 12 near its leading end and by which the tags are to be looped over the necks of bottles traveling along a conveyor line.

The carrier strip 10 is coated with a layer 14 of pressure-sensitive adhesive by which the tags 11 are secured to the strip. Each tag has a coating 15 of silicone or other release material on the face thereof secured to the carrier strip.

A leaflet 16 attachment is adhesively bonded to the upper face of the tag and overlies the tag entirely except for a narrow strip 11*a* at the trailing end of the tag. The leaflet is in this instance formed from a strip of paper material the leading part 17 of which is a single layer and overlies the corresponding part of the tag and the trailing part 18 of which is folded inward. The leading part 17 of the leaflet has an aperture in register with the aperture 12 in the tag and is secured to the tag by three parallel transversely extending lines of adhesive spaced apart along the length of the tag. Thus, there is a double thickness of paper about the neck of the bottle for strength while at the same time, the use of the transverse parallel lines of adhesive improves the flexibility of the leading part to facilitate the reeling of the strip. The trailing part 18 of the leaflet comprises a top part 19 which is a continuation of the leading part 17, a first continuation part 20 underlying the top part 19 and connected to the top part along a fold line 21, and a second continuation part 22 which is connected along a fold line 23 to the first continuation part and which lies between the top and first continuation parts. A transverse line of adhesive 24 extending along the trailing edge of the first continuation part 20 secures the trailing end of the leaflet to the tag. A line of perforations 25 is provided between the leading and trailing halves and when torn open allows access to the inner parts of the leaflet. These inner parts may or may not be separable from the outer parts, as desired.

Initially, the entire upper surface of the carrier strip is coated with adhesive 14 but the adhesive in the areas not covered by the tags is subsequently rendered inactive by a varnish applied to these areas and exposure thereof to ultra-violet light in a known manner, so that the strip carrying the tags can be formed into a roll. Preferably a narrow band extending under the periphery of the tag is similarly treated to render its adhesive inactive.

A notch 26 is formed in the top sheet 19 at each end of the line of perforations 25 and straddles the line so as to expose the location of the line.

Figure 5:
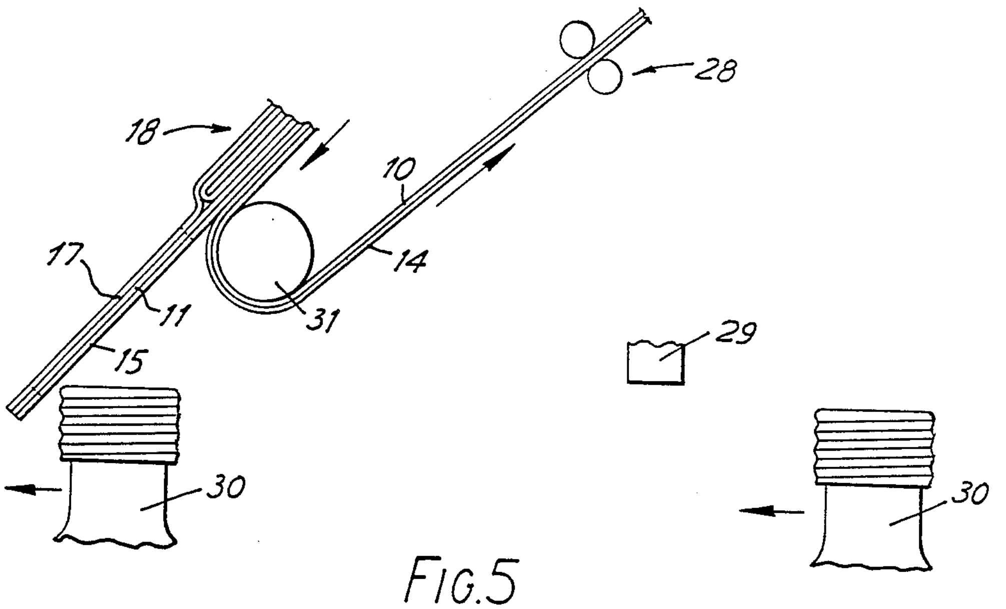
FIG. 5 illustrates a method according to the invention of employing the tag application system.

In use, referring now to FIG. 5, the strip is fed, with the apertured ends of the tags leading, along a downwardly inclined path towards the tops of a succession of bottles 30 standing on a conveyor and moving in the same general direction as the strip. At the lower end of the path is a roller 31 have a small diameter about which the strip is led, the tags being on the face of the strip remote from the roller.

At the downstream side of the guide roller the strip is engaged in a clutch and brake mechanism 28 which feeds the strip forward in a stepwise manner one tag at a time in response to a signal from a sensor 29 actuated by the passing of a container on the conveyor. When the clutch is thus operated, the strip beneath a tag commences to move about the roller, and the relative stiffness of the tag and the release material on its lower surface cause the tag 11 to commence to part from the strip 10. A bottle 30 on the conveyor is arranged to pass under the roller 30 at the same time so that its neck engages in the aperture in the tag and the tag with its leaflet is transferred to the neck of the bottle. The strip less the tags is fed to a take-up spool (not shown) and is discarded.

Figure 3:
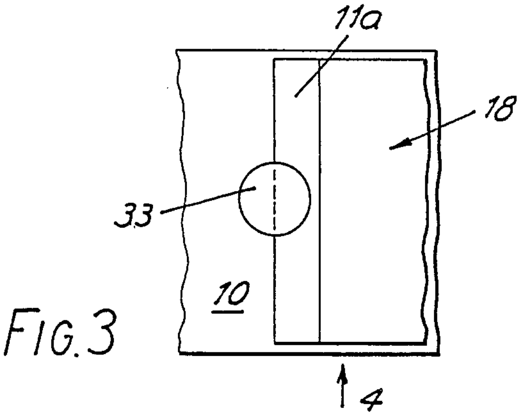
FIG. 3 is a fragmentary view similar to FIG. 1 of a tag in which an additional feature is incorporated.
Figure 4:
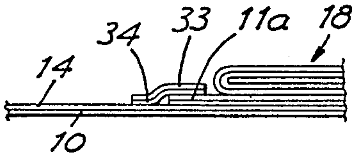
FIG. 4 is a side view taken in the direction of the arrow 4 of FIG. 3.

In a modification illustrated in FIGS. 3 and 4, a means is provided by which the trailing end of the tag can be adhesively secured to the bottle. A piece of paper material 33 carrying a pressure-sensitive adhesive 34 is placed partly overlapping and secured to the trailing end 11*a* of the tag, and the portion not attached to the tag is releasably bonded to a deactivated area of the strip, the varnish operating as a release material when the tag is detached from the strip so that the adhesive surface on the piece of paper material can be used to secure the trailing end of the tag to the bottle.

Figure 6:
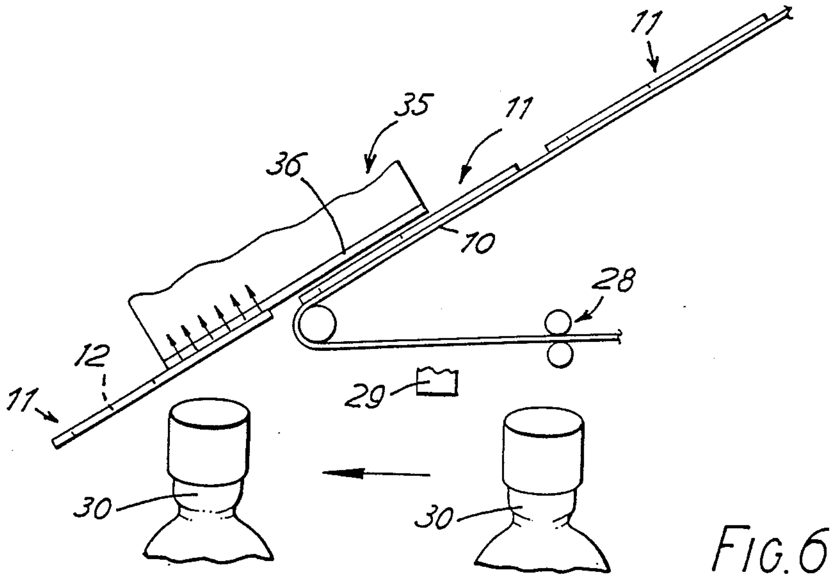
FIG. 6 illustrates a modification of the method illustrated in FIG. 5.

Referring now to FIG. 6, a modified form of the apparatus and method is illustrated. In this apparatus, a vacuum box 35 is disposed above the guide roller 31 and has an apertured bottom plate 36 which is inclined downward towards the tops of the containers. When a leading tag has become attached to its container, the mechanism 28 causes a forward step movement of the strip, and as the strip is drawn about the roller 31, the next tag peels off and becomes attached to the underside of the plate by suction generated in the vacuum box at the time that the apertured leading end of the tag projects beyond the plate and rests in the path of the top of a container. The neck of the container thus engages the tag in the aperture thereof and the tag becomes looped on the container. The container may pull the tag from the plate, overcoming the suction, or air may be blown into the vacuum box to discharge the tag from the plate, as desired.

Holes in the vacuum plate may be blocked off to define the area of which suction is required.

It will be understood that the leaflet may incorporate as many sheets as desired, may be in any desired form and may be detachably or non-detachably secured to the tag with or without detachable parts, or that the leaflet may be omitted entirely.

I claim:

1. A tag attachment system from which tags are suppliable to necked articles, said system comprising:

a strip of material having pressure-sensitive adhesive disposed on a portion of a surface thereof, and the remainder of the surface of said strip being non-adhesive;

a plurality of tags releasably secured to said strip at the portion of said surface thereof having adhesive and spaced apart along the length of said strip, each of said tags having a surface on which a layer of coating release material is disposed, and a first end through which an aperture extends for receiving the neck of a necked article, said release material being removable from said adhesive, and the surface of said tags covering the surface of said strip only at said portion thereof on which the pressure-sensitive adhesive is disposed whereby said release material facilitates the releasable securement of said tags to said strip.

2. A tag attachment system as claimed in claim 1, wherein each of said tags further includes a second end remote from said first end, and further comprising respective adhesive means connected to the second end of each of said tags for allowing the tags to be adhesively secured to necked articles once the necks of the articles are respectively received in the holes of the tags extending through the first ends thereof.

3. A tag attachment system as claimed in claim 2, wherein each said adhesive means comprises a portion of material having a surface on which pressure-sensitive adhesive is disposed extending from the second end of the tag, the surface of said portion of material confronting the remainder of the surface of the strip with the adhesive on the surface of said portion of material releasably securing said portion of material to said strip.

4. A tag application system as claimed in any one of claims 1–3, and further comprising a respective folded leaflet attached to each of said tags.

5. A tag attachment system as claimed in claim 4, and further comprising a respective cover sheet detachably secured to each of said tags at opposite ends of the folded leaflet attached to the tag and holding the folded leaflet in a closed state against the tag.

6. A tag attachment system as claimed in claim 1, and further comprising a respective folded leaflet secured to each of said tags, each said leaflet comprising a strip of paper including an outer portion having a leading end part secured to the tag and through which leading end an aperture extends in register with the hole extending through the first end of the tag and a trailing end part extending parallel to and spaced above the tag, and an inner portion connected to the trailing end part of the outer portion at a transverse fold line, the inner portion disposed between the tag and the outer portion of the leaflet, attached to the tag with adhesive at a location adjacent said fold line, and comprising a series of superposed panels underlying the outer portion and connected to one another at respective transverse fold lines extending parallel to one another and defined therebetween.

7. A tag attachment system as claimed in claim 6, wherein each of said leaflets includes a series of perforations extending therein linearly across said outer portion at an end of said trailing end part adjacent said leading end part.

8. A tag attachment system as claimed in claim 1, wherein a portion of material extends from the second end of each of said tags and has a surface thereof lying over said strip, the surface of said portion of material having adhesive that is releasable from the strip at the part thereof over which the surface of said portion of material lies.

* * * * *